United States Patent [19]
Hollands et al.

[11] Patent Number: 5,167,639
[45] Date of Patent: Dec. 1, 1992

[54] CATHETER ATTACHMENT DEVICE

[75] Inventors: Keith G. M. Hollands, Sompting; Graham E. Steer, Fulham, both of United Kingdom

[73] Assignee: E. R. Squibb & Sons, Inc., Princeton, N.J.

[21] Appl. No.: 548,031

[22] Filed: Jun. 22, 1990

[30] Foreign Application Priority Data

Jul. 19, 1989 [GB] United Kingdom ............... 8916495

[51] Int. Cl.$^5$ .............................................. A61M 5/32
[52] U.S. Cl. ........................... 604/180; 128/DIG. 26
[58] Field of Search ............. 604/174, 177, 179, 180; 128/DIG. 26

[56] References Cited

U.S. PATENT DOCUMENTS

| | | | |
|---|---|---|---|
| 2,590,006 | 3/1952 | Gordon | 604/180 |
| 3,339,546 | 9/1967 | Chen | 128/156 |
| 3,826,254 | 7/1974 | Mellor | 128/133 |
| 3,834,380 | 9/1974 | Boyd | 128/133 |
| 3,918,446 | 11/1975 | Buttaravoli | 604/180 |
| 3,990,454 | 11/1976 | Schlesinger | 604/180 |
| 4,025,015 | 5/1977 | Kolic | 248/205 A |
| 4,074,397 | 2/1978 | Rosin | 24/73 AS |
| 4,080,970 | 3/1978 | Miller | 128/350 R |
| 4,096,863 | 6/1978 | Kaplan et al. | 128/349 R |
| 4,122,857 | 10/1978 | Haerr | 128/348 |
| 4,170,995 | 10/1979 | Levine et al. | 604/180 |
| 4,192,785 | 3/1980 | Chen et al. | 128/283 |
| 4,276,882 | 7/1981 | Dickhudt et al. | 128/DIG. 26 X |
| 4,333,468 | 6/1982 | Geist | 128/348 |
| 4,336,806 | 6/1982 | Eldridge | 128/DIG. 26 X |
| 4,360,025 | 11/1982 | Edwards | 604/180 |
| 4,378,012 | 3/1983 | Brown | 128/207.17 |
| 4,392,857 | 12/1983 | Beran | 604/179 |
| 4,393,080 | 7/1983 | Pawelchak et al. | 428/355 |
| 4,397,647 | 8/1983 | Gordon | 604/180 |
| 4,416,664 | 11/1983 | Womack | 604/174 |
| 4,460,356 | 7/1984 | Moseley | 604/180 |
| 4,484,914 | 11/1982 | Brown | 604/180 |
| 4,527,559 | 7/1985 | Roxburg et al. | 128/207.17 |
| 4,533,349 | 8/1985 | Bark | 604/174 |
| 4,551,490 | 11/1985 | Doyle et al. | 524/22 |
| 4,571,245 | 2/1986 | Hubbard et al. | 604/179 |
| 4,586,919 | 5/1986 | Taheri | 604/9 |
| 4,617,017 | 10/1986 | Hubbard et al. | 604/179 |
| 4,645,492 | 2/1987 | Weeks | 604/174 |
| 4,662,873 | 5/1987 | Lash | 604/179 |
| 4,683,882 | 8/1987 | Laird | 128/200.26 |
| 4,699,616 | 10/1987 | Nowak et al. | 604/180 |
| 4,711,636 | 12/1987 | Bierman | 604/180 |
| 4,717,385 | 1/1988 | Cameron et al. | 604/174 |
| 4,762,738 | 9/1988 | Keyes et al. | 428/36 |
| 4,799,923 | 1/1989 | Campbell | 604/179 |
| 4,801,296 | 1/1989 | Vaillancourt | 604/272 |
| 4,822,342 | 4/1989 | Brawner | 604/180 |
| 4,830,914 | 5/1989 | Vaillancourt | 428/41 |
| 4,874,340 | 10/1989 | Hesketh | 604/180 |

FOREIGN PATENT DOCUMENTS

| | | |
|---|---|---|
| 206558 | 12/1986 | European Pat. Off. . |
| 2199499 | 7/1988 | United Kingdom . |
| 2211417 | 7/1989 | United Kingdom . |

*Primary Examiner*—C. Fred Rosenbaum
*Assistant Examiner*—Mark O. Polutta
*Attorney, Agent, or Firm*—Stephen B. Davis; Stuart E. Krieger

[57] ABSTRACT

A catheter attachment device comprises a first pad of medical grade adhesive having one surface covered by a removable protective layer, a second surface covered by a plastics film, and, attached to the film, a second pad of medical grade adhesive. A surface of this second pad which faces away from the first pad is covered by a removable protective layer and has a plastics film on its other surface. The two plastics films are attached to each other over a central region substantially smaller in area than the areas of both the first and second pads.

2 Claims, 2 Drawing Sheets

CATHETER ATTACHMENT DEVICE

BACKGROUND OF THE INVENTION

As a result of various medical procedures, catheters often are employed to drain body fluids or administer substances. Various devices have been developed for the purpose of securing a catheter or other tubing to the body of the patient to prevent accidental dislodgement. Devices which rely on an adhesive attachment to the catheter or tubing are shown, for example, by Mellor in U.S. Pat. No. 3,826,254, Haerr in U.S. Pat. No. 4,122,857, Geist in U.S. Pat. No. 4,333,468, Brown in U.S. Pat. No. 4,484,914, Moseley in U.S. Pat. No. 4,460,356, Vaillancourt in U.S. Pat. Nos. 4,801,296 and 4,830,914, Hesketh in U.K. patent application 2,211,417, and Muller in European patent application 206,558. Other devices have been developed which secure the catheter by a means of interengageable fabric such as Velcro as shown, for example, by Boyd in U.S. Pat. No. 3,834,380, Rosin in U.S. Pat. No. 4,074,397, Kaplan et al. in U.S. Pat. No. 4,096,863, Womack in U.S. Pat. No. 4,416,664, Hubbard et al. in U.S. Pat. Nos. 4,571,245 and 4,617,017 and Campbell in U.S. Pat. No. 4,799,923. Other devices have been developed which rely on a mechanical means to secure the catheter as shown, for example, by Edwards in U.S. Pat. No. 4,360,025, Brown in U.S. Pat. No. 4,378,012, Beran in U.S. Pat. No. 4,392,857, Gordon in U.S. Pat. No. 4,397,647, Taheri in U.S. Pat. No. 4,586,919, Weeks in U.S. Pat. No. 4,645,492, Nowak et al. in U.S. Pat. No. 4,699,616, Bierman in U.S. Pat. No. 4,711,636, Cameron et al. in U.S. Pat. No. 4,717,385, and Hesketh in U.S. Pat. No. 4,874,380.

SUMMARY OF THE INVENTION

According to the present invention, there is provided a catheter attachment device comprising a first pad of medical grade adhesive having one surface covered by a removable protective layer, a second surface covered by a plastics film, and, attached to the film, a circular or near-circular pad of medical grade adhesive (herein called a second pad) having its surface which faces away from the first pad covered by a removable protective layer and a plastics film on its other surface, the two plastics films being attached to each other over a central region substantially smaller in area than the areas of both the first and second pads.

In an advantageous embodiment of the invention, the visible surface of the second pad, or the visible surface of a removable protective layer thereon carries a number of arrows pointing in radially outward directions. The purpose of these arrows is to indicate to the user that the catheter can be oriented relative to the catheter attaching device in any radial direction.

DETAILED DESCRIPTION OF THE INVENTION

There is a need for a simple and inexpensive catheter attachment device which permits a catheter to be readily attached to the body of a patient in any one of a plurality of orientations relative to the patient. In contrast to the present invention, all simple conventional catheter attachment devices, once attached to the skin, permit only one stable orientation for the catheter.

Figure 1:
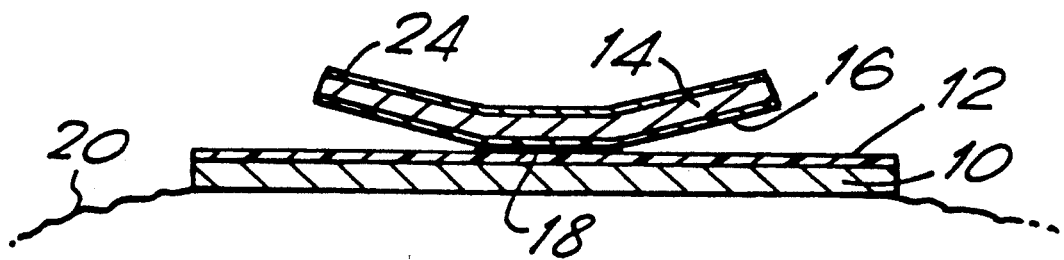
FIG. 1 is a vertical cross-section through one example of catheter attaching device according to the invention, taken on the line indicated I—I in FIG. 3.
Figure 2:
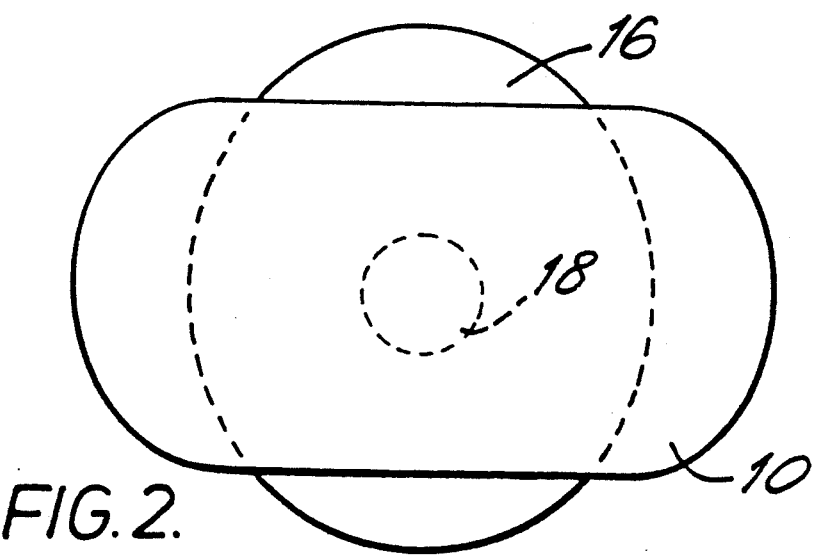
FIG. 2 is an underplan view of the device shown in FIG. 1 but with the removable protective layer removed from the undersurface of the first pad.
Figure 3:
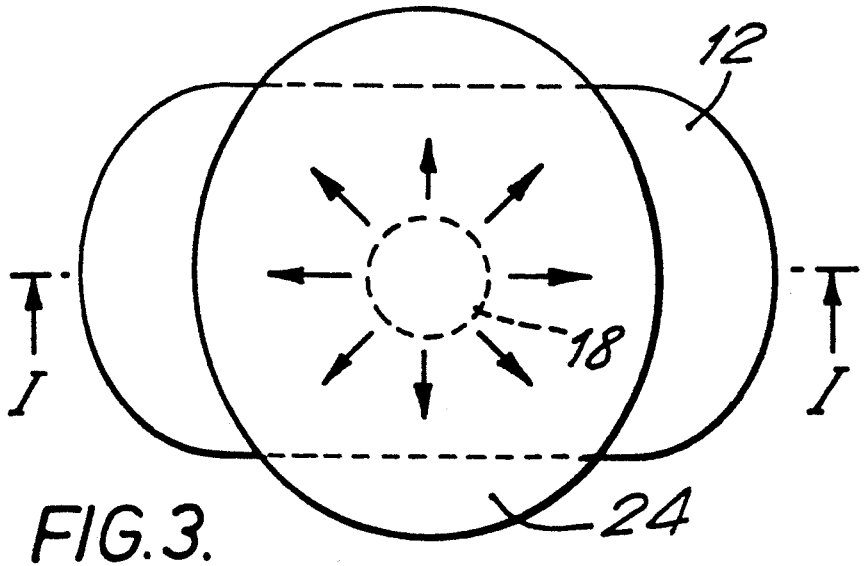
FIG. 3 is a plan view of the device shown in FIGS. 1 and 2.

The illustrated catheter attaching device includes a first pad 10 of medical grade adhesive material which has on one surface a removable protective layer (not shown) and a second surface covered by a plastics film 12. A circular or near-circular second pad of medical grade adhesive material is shown at 14 and has on one surface a removable protective layer 24 and on the other surface a plastic film 16. These pads are permanently connected to one another in any suitable manner over a join zone 18. For example, the two plastics films 12 and 16 may be heat welded or radio frequency welded together, or the two pads may be secured by an adhesive over the join zone 18 which is strong enough to connect them permanently. As will be seen, the join zone 18 occupies a central region of each pad and the central region is substantially smaller in area than the areas of both the first and the second pads. A consequence of this is that the marginal regions of the second pad can readily be lifted away from the film 12 on the first pad. Although as illustrated in FIG. 1 the join area is shown as a central region having a diameter about one third the diameter of the second pad 14, in many practical constructions of catheter attaching device, the join area will be smaller than illustrated in FIG. 1.

Any of the known medical grade pressure sensitive adhesives can be employed as the first and second pads. Preferably, adhesive materials 10 and 14 are formulated by blending one or more water soluble or swellable hydrocolloids with a polyisobutylene or a mixture of polyisobutylenes or a mixture of one or more polyisobutylenes and one or more non-acrylic elastomers. Other materials can be included within the adhesive formulations such as mineral oil, tackifiers, antioxidants, cohesive strengthening agents, and pharmaceutically active materials such as anti-inflammatory agents, antiseptics, or materials having skin healing or soothing properties. Suitable adhesive formulations are taught by Chen in U.S. Pat. No. 3,339,546, Chen et al. in U.S. Pat. No. 4,192,785, Pawelchak et al. in U.S. Pat. No. 4,393,080, Doyle et al. in U.S. Pat. No. 4,551,490, and by Keyes et al. in U.S. Pat. No. 4,762,738. As disclosed in these references, suitable water soluble and water swellable hydrocolloids include sodium carboxymethylcellulose, pectin, gelatin, guar gum, locust bean gum, gum karaya, and mixtures thereof. Suitable cohesive strengthening agents include water-insoluble cross-linked sodium carboxymethylcellulose, water-insoluble cross-linked dextran, etc. Suitable non-acrylic elastomers include butyl rubber and styrene radial or block copolymers such as styrene-butadiene-styrene (S-B-S) and styrene-isoprene-styrene (S-I-S) block type copolymers.

Figure 4:
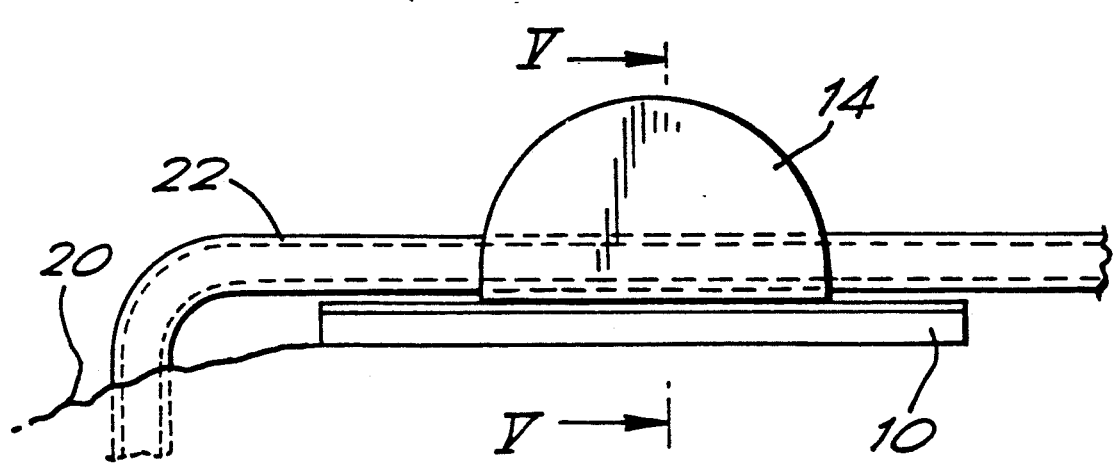
FIG. 4 is a side elevation view showing the catheter attaching device according to this embodiment of the invention in a typical position of use.
Figure 5:
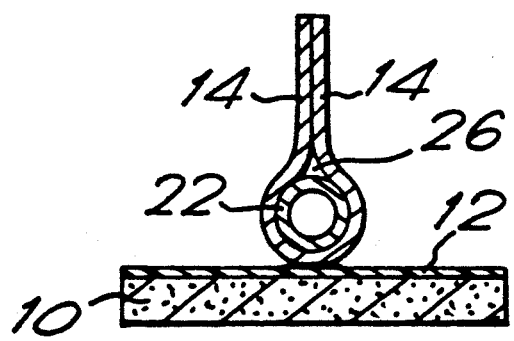
FIG. 5 is a cross-sectional view of the device on the line V—V in FIG. 4.

Referring now to FIGS. 4 and 5, there is shown the medical grade adhesive pad 10 attached to the skin 20 of a patient, and a catheter 22, draining body fluid (e.g., urine) from the patient is shown at 22. The patch 10 is attached to the skin of the wearer in any desired orientation as may be convenient for the nurse, after the removable cover layer has been stripped off. Thereafter, the catheter is laid over the second adhesive pad 14. It is to be particularly noted that the catheter 22 can extend in any radial direction with reference to the second pad 14, without necessitating a change of the positioning or orientation of the first pad 10 on the skin of the patient. This is a considerable advantage to nurses in practice. Then, the nurse places her fingers under the marginal regions of the second pad 14 and lifts and pinches it together (after the removable cover layer 24 has been removed) so that it takes up the position indicated in FIG. 5 with the two exposed surfaces of the medical grade adhesive sticking firmly to one another and firmly holding the catheter in position. If it is later desired to remove the catheter then by inserting one blade of a scissors through the space indicated at 26 in FIG. 5 a cut may be made in the pad 14 and the catheter readily removed. Since the catheter attachment device disclosed and illustrated is very simple in design and very cheap to manufacture, such devices can be thrown away after use.

As will be appreciated, it is a considerable advantage that the nurses or other person caring for the patient does not have to take special care in positioning the first pad 10 on the skin of the patient. It may be located in any orientation because the catheter can be arranged to extend across the second pad 14 in any desired radial direction. Irrespective of the direction, the catheter can be firmly retained by pinching together the two portions of the second pad 14 as illustrated in FIG. 5.

A man skilled in the art will appreciate that it is possible to make modifications to the device particularly disclosed and illustrated without departing from the invention. While the pad 10 has been illustrated as generally rectangular with rounded corners, it could be oval or any other desired shape. While the pad 14 has been illustrated as circular or near circular, it could be oval providing the length of the minor axis is about 75% or more of the length of the major axis. For some medical adhesive materials, the plastics layers 12 and 16 may be omitted. Also, the attachment device of this invention is useful for securing to the patient other types of tubing, wires, etc., in addition to drainage catheters, as may be needed.

What is claimed is:

1. A catheter attachment device comprising:
   a first pad of medical grade adhesive having a first surface for attachment to a user's skin, said first surface covered by a removable protective layer, and a second surface opposing said first surface covered by a plastics film, and
   a substantially circular second pad of medical grade adhesive attached to the first pad, said second pad having a surface for securing a catheter, said catheter securing surface facing away from said first pad and covered by a removable protective layer, said second pad having a plastics film on the other surface thereof, the two plastics films being hingedly secured to each other at the center of said substantially circular second pad, said two plastic films being unattached in the annular space around said center whereby said second pad may be folded substantially symmetrically about a catheter placed thereon across said center regardless of the angular orientation of said catheter to said first or second pad.

2. A device according to claim 1 in which the second pad is circular.

* * * * *